US009732134B2

(12) United States Patent
Gavin et al.

(10) Patent No.: US 9,732,134 B2
(45) Date of Patent: Aug. 15, 2017

(54) METHOD OF TREATING GRAFT VERSUS HOST DISEASE USING IL-2 MUTEINS

(71) Applicant: Amgen Inc., Thousand Oaks, CA (US)

(72) Inventors: Marc A Gavin, Vashon, WA (US); Li Li, Sammamish, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/672,417

(22) Filed: Nov. 8, 2012

(65) Prior Publication Data

US 2013/0195795 A1     Aug. 1, 2013

Related U.S. Application Data

(63) Continuation of application No. 13/145,537, filed as application No. PCT/US2010/021519 on Jan. 20, 2010, now abandoned.

(60) Provisional application No. 61/146,111, filed on Jan. 21, 2009.

(51) Int. Cl.
    *A61K 38/20*      (2006.01)
    *C07K 14/55*      (2006.01)
    *A61K 38/00*      (2006.01)

(52) U.S. Cl.
    CPC ............. *C07K 14/55* (2013.01); *A61K 38/00* (2013.01)

(58) Field of Classification Search
    CPC ................................ C07K 14/55; A61K 38/00
    USPC ......................................... 424/85.2; 435/375
    See application file for complete search history.

(56) References Cited

U.S. PATENT DOCUMENTS

| | | |
|---|---|---|
| RE33,653 E | 7/1991 | Mark et al. |
| 6,348,192 B1 | 2/2002 | Chan et al. |
| 6,737,056 B1 | 5/2004 | Presta et al. |
| 6,927,043 B2 | 8/2005 | Chan et al. |
| 6,955,807 B1 | 10/2005 | Shanafelt et al. |
| 7,091,321 B2 | 8/2006 | Gillies et al. |
| 7,105,653 B2 | 9/2006 | Shanafelt et al. |
| 7,371,371 B2 | 5/2008 | Epstein et al. |
| 7,507,406 B2 | 3/2009 | Gillies et al. |
| 7,514,073 B2 | 4/2009 | Epstein et al. |
| 7,569,215 B2 | 8/2009 | Wittrup et al. |
| 7,790,415 B2 | 9/2010 | Gillies et al. |
| 7,803,361 B2 | 9/2010 | Epstein et al. |
| 7,888,071 B2 | 2/2011 | Gillies et al. |
| 8,124,066 B2 | 2/2012 | Epstein et al. |
| 8,592,562 B2 | 11/2013 | Kannan et al. |
| 2005/0142106 A1 | 6/2005 | Wittrup et al. |
| 2010/0286374 A1 | 11/2010 | Kannan et al. |
| 2011/0150826 A1 | 6/2011 | Paulsen et al. |

FOREIGN PATENT DOCUMENTS

| | | |
|---|---|---|
| EP | 0506124 A1 | 3/1992 |
| EP | 1252192 B1 | 8/2006 |
| EP | 2288372 B1 | 2/2012 |
| WO | WO90/00565 A1 | 1/1990 |
| WO | WO99/60128 A1 | 11/1999 |
| WO | 2004/082681 A1 | 9/2004 |
| WO | WO2005/086751 A2 | 9/2005 |
| WO | WO2005/086798 A2 | 9/2005 |
| WO | WO2007/095643 A2 | 8/2007 |
| WO | 2007/100770 A2 | 9/2007 |
| WO | 2008/062158 A2 | 5/2008 |
| WO | 2008/106116 A2 | 9/2008 |
| WO | 2009/061853 A2 | 5/2009 |
| WO | WO2009/061853 A2 | 5/2009 |
| WO | WO 2009/135615 A2 | 11/2009 |
| WO | WO2010017220 A1 | 2/2010 |
| WO | 2010/085495 A1 | 7/2010 |
| WO | 2012/125850 A1 | 9/2012 |
| WO | WO2012123381 A1 | 9/2012 |

OTHER PUBLICATIONS

Boyman et al., "Selective Stimulation of T Cell Subsets with Antibody-Cytokine Immune Complexes", Science, 311:1924-1927, 2006.
Boyman et al., "Potential use of IL-2/anti-IL-2 antibody immune complexes for the treatment of cancer and autoimmune disease", Expert Opin. Biol. Ther. 6(12):1325-1331, 2006.
Collins et al., "Identification of specific residues of human interleukin 2 that affect binding to the 70-kDa subunit (p70) of the interleukin 2 receptor", Proc. Natl. Acad. Sci. USA, 85:7709-7713, 1988.
Finkelman et al., "Anti-Cytokine Antibodies as Carrier Proteins", J. Immunol. 151(3):1235-1244, 1993.
Fujii et al., "Activation of Stat5 by interleukin 2 requires a carboxyl-terminal region of the interleukin 2 receptor beta chain but is not essential for the proliferative signal transmission," PNAS 92:5482 5486, 1995.
Hartmann, Gunther, "Technology evaluation: BAY-50-4798, Bayer", Current Opinion in Molecular Therapeutics, 6 (2):221-227 + 684, 2004.
Koreth et al., "Interleukin-2 and Regulatory T Cells in Graft-versus-Host Disease", The New England Journal of Medicine, 365(22):2055-2066, 2011.
Lan et al., "The regulatory, inflammatory, and T cell programming roles of interleukin-2 (IL-2)," J Autoimmun 31:7-12, 2008.
Malek, "The biology of interleukin-2," Annu Rev Immunol 26:453-479, 2008.
Nagase et al., "Despite increased CD4+Foxp3+ cells within the infection site, BALB/c IL-4 receptor-deficient mice reveal CD4+Foxp3-negative T cells as a source of IL-10 in Leishmania major susceptibility," J Immunol 179:2435-2444, 2007.
Rao et al., "High-affinity CD25-binding IL-2 mutants potently stimulate persistent T cell growth," Biochemistry 44:10696-10701, 2005.
Sasaoki et al., "Deamidation at asparagine-88 in recombinant human interleukin 2," Chem Pharm Bull 40(4):976-980, 1992.
Shanafelt et al., "A T-cell selective interleukin 2 mutein exhibits potent antitumor activity and is well tolerated in vivo," Nat Biotechnol 18:1197-1202, 2000.

(Continued)

*Primary Examiner* — Prema Mertz
(74) *Attorney, Agent, or Firm* — Lawrence B. Kong

(57) ABSTRACT

Described herein are immunosuppressive molecules including immunosuppressive variants of IL-2, and use of such molecules to treat inflammatory and autoimmune disorders.

3 Claims, 8 Drawing Sheets

(56) References Cited

OTHER PUBLICATIONS

Tang et al., "Central role of defective interleukin-2 production in the triggering of islet autoimmune destruction," Immunity 28:687-697, 2008.
Thanos et al., "Hot-Spot mimicry of a cytokine receptor by a small molecule", PNAS, 103(42):15422-15427, 2006.
Wang et al., "Structure of the quaternary complex of interleukin-2 with its α, β, and γ c receptors," Science 310:1159-1163, 2005.
Rizzieri et al. "Feasibility of low dose interleukin-2 therapy following T cell-depleted non-myeloablative allogeneic hematopoietic stem cell transplantation from HLA matched or mismatched family member donors", Cancer Invest. 2011, 29(1): 56-61.
Fell et al., Genetic construction and characterization of a fusion protein consisting of a chimeric F(ab') with specificity for carcinomas and human IL-2, Apr. 1991, J. Immunol, vol. 146(7); 2446-52.
Fujii et al., Activation of Stat5 by interleukin 2 requires a carboxyl-terminal region of the interleukin 2 receptor beta chain but is not essential for the proliferative signal transmission, 1995, PNAS 92:5482-5486.
Gillessen et al., A phase I dose-escalation study of the immunocytokine EMD 521873 (Selectikine) in patients with advanced solid tumours, Jan. 2013, Eur J Cancer, vol. 49(1); 35-44.
Gillies et al. Biological activity and in vivo clearance of antitumor antibody/cytokine fusion proteins, May/Jun. 1993, Bioconjug Chem, vol. 4(3); 230-5.
Gillies et al., A low-toxicity IL-2-based immunocytokine retains antitumor activity despite its high degree of IL-2 receptor selectivity, Jun. 2011, Clin. Cancer Res., vol. 17(11); 3673-85.
Gillies et al., Antibody-targeted interleukin 2 stimulates T-cell killing of autologous tumor cells, Feb. 1992, Proc Natl Acad Sci U.S.A., vol. 89(4); 1428-32.
Gillies et al., Improved circulating half-life and efficacy of an antibody-interleukin 2 immunocytokine based on reduced intracellular proteolysis, Jan. 2002, Clin. Cancer Res, vol. 8(1); 210-6.
Jung et al., Aglycosylated IgG variants expressed in bacteria that selectively bind FcyRI potentiate tumor cell killing by monocyte-dendritic cells, Jan. 12, 2010, PNAS, vol. 107, 604-609.
Kendra et al., Pharmacokinetics and stability of the ch14.18-interleukin-2 fusion protein in mice, Aug. 1999, Cancer Immunol Immunother, vol. 48(5), 219-29.
King et al., Phase I clinical trial of the immunocytokine EMD 273063 in melanoma patients, Nov. 2004, J. Clin. Oncol., vol. 22(22); 4463-73.
Ko et al., Safety, pharmacokinetics, and biological pharmacodynamics of the immunocytokine EMD 273066 (huKS-IL2): results of a phase I trial in patients with prostate cancer, May/Jun. 2004, J Immunother, vol. 27(3); 233-239.
Laurent et al., T-cell activation by treatment of cancer patients with EMD 521873 (Selectikine), an IL-2/anti-DNA fusion protein, Jan. 2013, vol. 11, 5.
Margolin et al., Phase I trial of BAY 50/4798, an interleukin-2-specific agonist in advanced melanoma and renal cancer, Jun. 2007, Clin. Cancer Res, vol. 13(11), 3312-9.
Matthews et al., BAY 50/4798, a novel, high-affinity receptor-specific recombinant interleukin-2 analog, induces dose-dependent increases in CD25 expression and proliferation among unstimulated, human peripheral blood mononuclear cells in vitro, Dec. 2004, Clin. Immunol., vol. 113(3); 248-55.
Nagase et al., Despite increased CD4+Foxp3+ cells within the infection site, BALB/c IL-4 receptor-deficient mice reveal CD4+ F oxp3-negative T cells as a source oflL-1 0 in Leishmania major susceptibility, 2007, J Immunol, 179:2435-2444.
Rao et al., High-affinity CD25-binding IL-2 mutants potently stimulate persistent T cell growth, 2005, Biochemistry 44:10696-10701.
Sasaoki et al., Deamidation at asparagine-88 in recombinant human interleukin 2, 1992, Chem Pharm Bull 40(4):976-980.
Shanafelt et al., A T-cell-selective interleukin 2 mutein exhibits potent antitumor activity and is well tolerated in vivo, Nov. 2000, Nat. Biotechnol., vol. 18(11); 1197-1202.
Steppan et al., Reduced secondary cytokine induction by BAY 50/4798, a high-affinity receptor-specific interleukin-2 analog, Mar. 2006, J. Interferon Cytokine Res., vol. 26(3); 171-8.
Tang et al., Central role of defective interleukin-2 production in the triggering of islet autoimmune destruction, 2008, Immunity 28:687-697.

FIG. 1

10 nM IL-2 variant:

100 pM IL-2 variant:

10 nM IL-2 variant:

100 pM IL-2 variant:

10 nM IL-2 variant:

100 pM IL-2 variant:

10 nM IL-2 variant:

100 pM IL-2 variant:

10 nM IL-2 variant:

100 pM IL-2 variant:

METHOD OF TREATING GRAFT VERSUS HOST DISEASE USING IL-2 MUTEINS

CROSS-REFERENCE TO RELATED APPLICATIONS

This application is a continuation of U.S. patent application Ser. No. 13/145,537, which is a National Stage application under 35 U.S.C. §371 of International Application No. PCT/US2010/021519 (which designated the United States), having an international filing date of Jan. 20, 2010, which is incorporated herein by reference in its entirety, which claims priority to U.S. Provisional Patent Application No. 61/146,111, filed Jan. 21, 2009.

REFERENCE TO THE SEQUENCE LISTING

The present application is being filed along with a Sequence Listing in electronic format. The Sequence Listing is provided as a file entitled A-1474-US-CNT_Seqlisting_ST25.txt, created Nov. 7, 2012, which is 13 KB in size. The information in the electronic format of the Sequence Listing is incorporated herein by reference in its entirety.

BACKGROUND

IL-2 binds three transmembrane receptor subunits: IL-2Rβ and IL-2Rγ which together activate intracellular signaling events upon IL-2 binding, and CD25 (IL-2Rα) which serves to present IL-2 to the other 2 receptor subunits. The signals delivered by IL-2Rβγ include those of the PI3-kinase, Ras-MAP-kinase, and STAT5 pathways.

T cells require expression of CD25 to respond to the low concentrations of IL-2 that typically exist in tissues. T cells that express CD25 include both $CD4^+$ $FOXP3^+$ regulatory T cells (T-reg cells)—which are essential for suppressing autoimmune inflammation—and $FOXP3^-$ T cells that have been activated to express CD25. $FOXP3^-$ $CD25^+$ T effector cells (T-eff) may be either $CD4^+$ or $CD8^+$ cells, both of which can be pro-inflammatory and may contribute to autoimmunity, organ graft rejection or graft-versus-host disease. IL-2-stimulated STAT5 signaling is crucial for normal T-reg cell growth and survival and for high FOXP3 expression.

Because of the low affinity IL-2 possesses for each of the three IL-2R chains, a further reduction in affinity for IL-2Rβ and/or IL-2Rγ could be offset by an increased affinity for CD25. Mutational variants of IL-2 have been generated that exhibit up to 170-fold higher affinity for CD25 (US Patent Application Publication No. 2005/0142106; Rao et al., *Biochemistry* 44, 10696-701 (2005)). These variants were reported to associate for several days with cell surface CD25 and to chronically promote growth of an IL-2-dependent cell line. The authors report that the mutants stimulate persistent T cell growth and, thus, may be useful in methods of viral immunotherapy and in treating cancer or other hyperproliferative disorders. High doses of IL-2 (Proleukin) are administered to cancer patients to induce anti-tumor immunity, a treatment that is often associated with undesirable toxicity. U.S. Pat. No. 6,955,807 describes IL-2 variants that are said to have reduced toxicity. The patent attributes the toxicity to IL-2-induced stimulation of natural killer (NK) cells, which only express IL-2Rβ and IL-2Rγ. The IL-2 variants described therein were said to have reduced toxicity because they selectively activate $CD25^+$ T cells over NK cells. Again the IL-2 variants were said to be useful in therapeutic methods wherein it is beneficial to generally stimulate the immune system, e.g., the treatment of cancer or infectious diseases.

SUMMARY

Provided herein are immunosuppressive mutational variants of IL-2 that preferentially promote the growth/survival of $FOXP3^+$ regulatory T cells (T-reg cells) over the growth/survival of potentially proinflammatory $FOXP3^-$ $CD25^+$ T cells. By increasing the ratio of T-reg to other T cells and/or by increasing FOXP3 expression in T-reg without activating $FOXP3^-$ $CD25^+$ T cells, these variants should suppress undesirable inflammation.

The unique properties of these IL-2 variants stem from two sets of mutations. One set of mutations results in a reduced affinity for the signaling chains of the IL-2 receptor (IL-2Rβ/CD122 and/or IL-2Rγ/CD132) and/or a reduced capacity to induce a signaling event from one or both subunits of the IL-2 receptor. The second set of mutations confers higher affinity for CD25 (IL-2Rα) and may include mutations described by Rao et al. (US Patent Application Publication No. 2005/0142106).

As described herein, certain IL-2 variants induce signaling events that preferentially induce survival, proliferation, activation and/or function of T-reg cells. In certain embodiments, the IL-2 variant retains the capacity to stimulate, in T-reg cells, STAT5 phosphorylation and/or phosphorylation of one or more of signaling molecules downstream of the IL-2R, e.g., p38, ERK, SYK and LCK. In other embodiments, the IL-2 variant retains the capacity to stimulate, in T-reg cells, transcription or protein expression of genes or proteins, such as FOXP3 or IL-10, that are important for T-reg cell survival, proliferation, activation and/or function. In other embodiments, the IL-2 variant exhibits a reduced capacity to stimulate endocytosis of IL-2/IL-2R complexes on the surface of $CD25^+$ T cells. In other embodiments, the IL-2 variant demonstrates inefficient, reduced, or absence of stimulation of PI3-kinase signaling, such as inefficient, reduced or absent phosphorylation of AKT and/or mTOR (mammalian target of rapamycin). In yet other embodiments, the IL-2 variant retains the ability of wt IL-2 to stimulate STAT5 phosphorylation and/or phosphorylation of one or more of signaling molecules downstream of the IL-2R in T-reg cells, yet demonstrates inefficient, reduced, or absent phosphorylation of STAT5, AKT and/or mTOR or other signaling molecules downstream of the IL-2R in $FOXP3^-$ $CD4^+$ or $CD8^+$ T cells or NK cells. In other embodiments, the IL-2 variant is inefficient or incapable of stimulating survival, growth, activation and/or function of $FOXP3^-$ $CD4^+$ or $CD8^+$ T cells or NK cells.

Provided are methods of treating an inflammatory or autoimmune disorder. The methods comprise administering a therapeutically effective amount of one or more immunosuppressive IL-2 variants to a subject.

Further provided are methods of promoting proliferation, survival, growth, or activation of regulatory T cells. The methods comprising contacting a FOXP3-positive ($FOXP3^+$) T cell with an immunosuppressive IL-2 variant.

Also provided is the use of an immunosuppressive IL-2 variant in the preparation of a medicament for the treatment of an inflammatory or autoimmune disorder.

Also provided are compositions of IL-2 variants conjugated to additional protein sequences or other chemical that prolong the stability and/or half-life of the therapeutic in vivo.

BRIEF EXPLANATION OF THE DRAWINGS

FIG. 1. Sequences of IL-2 variants. Sequences that vary from germline human IL-2 are not shaded in gray.

FIG. 2A An example of flow cytometric data and gating strategy. Representative data is shown in FIG. 1A where 9.5% of CD4+ cells are CD25+FOXP3+, 9.9% of CD4− cells are CD25+FOXP3− and 6.7% of CD8+ cells are CD25+FOXP3−. FOXP3+CD8+ T cells are typically very infrequent. FIG. 2B. Relative number of CD8+CD25+ FOXP3− T cells. FIG. 2C. Relative number of CD4+CD25+ FOXP3− T cells. FIG. 2D. Relative number of CD4+CD25+ FOXP3+ T cells. FIG. 2E. Ratio of FOXP3+/FOXP3− cells among CD25+CD4+ T cells. FIG. 2F. IL-2-mediated FOXP3 upregulation in FOXP3+CD4+ T cells.

DETAILED DESCRIPTION OF PREFERRED EMBODIMENTS

Figure 2A:
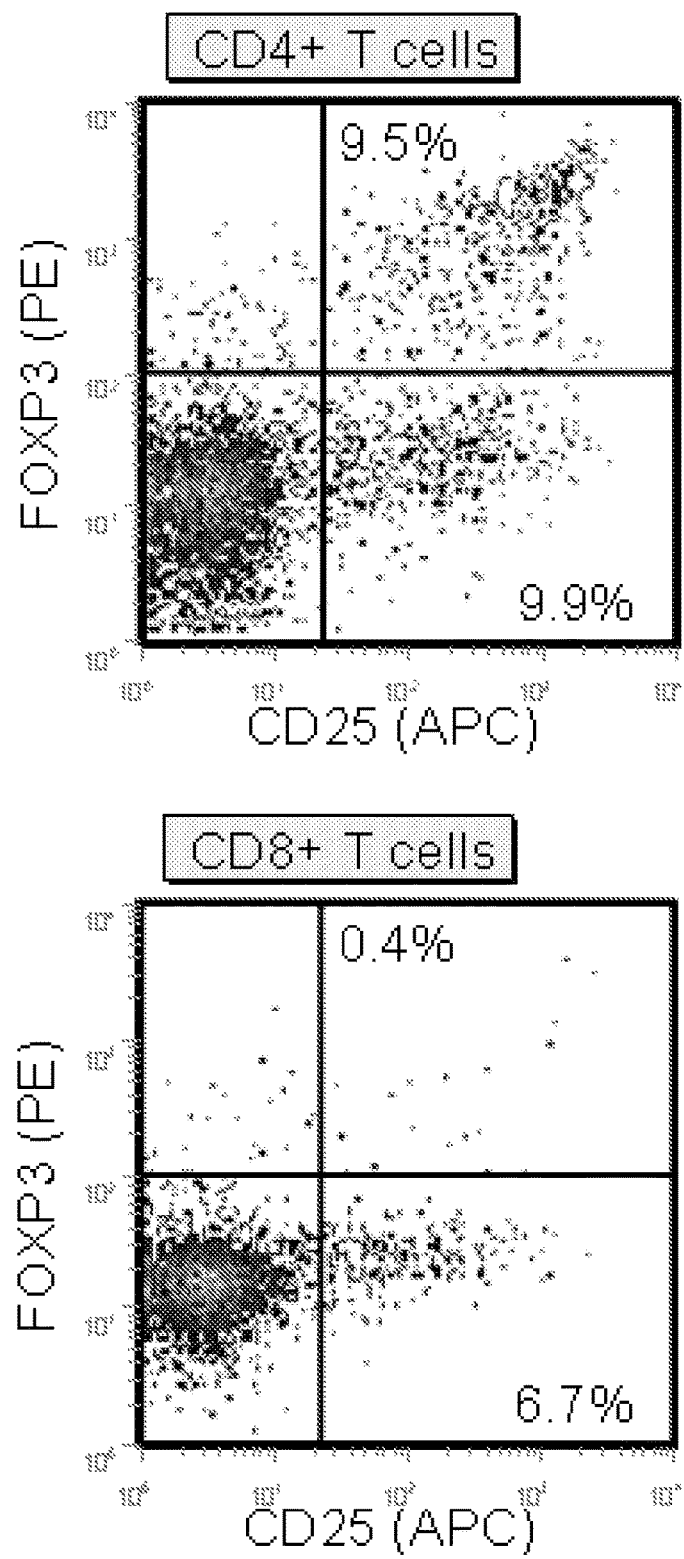
FIG. 2A-2F.

FOXP3+ regulatory T cells (T-reg cells) are essential for maintaining normal immune homeostasis and immune tolerance to self tissues, as well as for suppressing undesirable inflammation. T-reg cells exert their suppressor and regulatory functions through multiple mechanisms which are likely to be regulated by temporal and environmental factors. Current immunosuppressive therapeutics generally target individual proinflammatory pathways and as such often exhibit partial efficacy or are applicable to specific diseases. An alternative immunosuppressive modality might involve the elevation of the numbers and activation state of natural suppressor cells to better enable them to deliver appropriate suppressor molecules/activities at sites of inflammation.

Described herein are therapeutic agents that selectively promote T-reg cell proliferation, survival, activation and/or function. By "selectively promote," it is meant the therapeutic agent promotes the activity in T-reg cells but has limited or lacks the ability to promote the activity in non-regulatory T cells. Further described herein are assays to screen for agents that selectively promote T-reg cell proliferation, survival, activation and/or function. Agents that may be screened include, but are not limited to, small molecules, peptides, polypeptides, proteins including antibodies, e.g., monoclonal, humanized, human, monovalent, bivalent, and multivalent antibodies.

In certain embodiments, the agent is an IL-2 variant. In particular, the IL-2 variant promotes these activities of T-reg cell growth/survival but have a reduced ability, as compared to wild-type IL-2, to promote non-regulatory T-cell (FOXP3− CD25+) and NK cell proliferation, survival, activation and/or function. In certain embodiments, such IL-2 variants function through a combination of elevated affinity for the IL-2R subunit IL-2Rα (CD25) and a reduced affinity for the signaling subunits IL-2Rβ and/or IL-2Rγ. Whereas IL-2 and variants thereof have been used in the art as immunostimulatory agents, e.g., in methods of treating cancer or infectious diseases, the IL-2 variants described herein are particularly useful as immunosuppressive agents, e.g., in methods of treating inflammatory disorders.

IL-2 variants comprise a sequence of amino acids at least 70%, at least 75%, at least 80%, at least 85%, at least 90%, at least 91%, at least 92%, at least 93% at least 94%, at least 95%, at least 96%, at least 97%, at least 98%, at least 99% identical to wild-type IL-2. IL-2 variants further include a sequence of amino acids at least 70%, at least 75%, at least 80%, at least 85%, at least 90%, at least 91%, at least 92%, at least 93% at least 94%, at least 95%, at least 96%, at least 97%, at least 98%, at least 99% identical to a functional fragment of wild-type IL-2. As used herein, "wild-type IL-2" shall mean the polypeptide having the following amino acid sequence:

```
                                      (SEQ ID NO: 1)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFXQSIISTLT
wherein X is C, S, A or V.
```

Variants may contain one or more substitutions, deletions, or insertions within the wild-type IL-2 amino acid sequence. Residues are designated herein by the one letter amino acid code followed by the IL-2 amino acid position, e.g., K35 is the lysine residue at position 35 of SEQ ID NO:1. Substitutions are designated herein by the one letter amino acid code followed by the IL-2 amino acid position followed by the substituting one letter amino acid code, e.g., K35A is a substitution of the lysine residue at position 35 of SEQ ID NO:1 with an alanine residue.

In one aspect, the invention provides immunosuppressive IL-2 variants that have a higher affinity for IL-2Rα than wild-type IL-2. U.S. Published Patent Application No. 2005/0142106 (incorporated herein by reference in its entirety) describes IL-2 variants that have higher affinity for IL-2Rα than does wild-type IL-2 and methods of making and screening for such variants. Preferred IL-2 variants contain one or more mutations in positions of the IL-2 sequence that either contact IL-2Rα or alter the orientation of other positions contacting IL-2Rα, resulting in higher affinity for IL-2Rα. The mutations may be in or near areas known to be in close proximity to IL-2Rα based on published crystal structures (Xinquan Wang, Mathias Rickert, K. Christopher Garcia. Science 310:1159 2005). IL-2 residues believed to contact IL-2Rα include K35, R38, F42, K43, F44, Y45, E61, E62, K64, P65, E68, V69, L72, and Y107.

IL-2 variants having greater affinity for IL-2Rα can include a change in N29, N30, Y31, K35, T37, K48, E68, V69, N71, Q74, S75, or K76. Preferred variants include those having one or more of the following mutations: N29S, N30S, N30D, Y31H, Y31S, K35R, T37A, K48E, V69A, N71R, and Q74P.

Immunosuppressive IL-2 variants also include variants that demonstrate altered signaling through certain pathways activated by wild-type IL-2 via the IL-2R and result in preferential proliferation/survival/activation of T-reg. Molecules known to be phosphorylated upon activation of the IL-2R include STAT5, p38, ERK, SYK, LCK, AKT and mTOR. Compared to wild-type IL-2, the immunosuppressive IL-2 variant can possess a reduced PI3K signaling ability in FOXP3− T cells, which can be measured by a reduction in the phosphorylation of AKT and/or mTOR as compared to wild-type IL-2. Such variants may include mutations in positions that either contact IL-2Rβ or IL-2Rγ or alter the orientation of other positions contacting IL-2Rβ or IL-2Rγ. IL-2 residues believed to contact IL-2Rβ include L12, Q13, H16, L19, D20, M23, R81, D84, S87, N88, V91, 192, and E95. IL-2 residues believed to contact IL-2Rγ include Q11, L18, Q22, E110, N119, T123, Q126, S127, I129, S130, and T133. In certain embodiments, the IL-2 variant comprises a mutation at E15, H16, Q22, D84, N88, or E95. Examples of such mutations include E15Q, H16N, Q22E, D84N, N88D, and E95Q.

Figure 1:
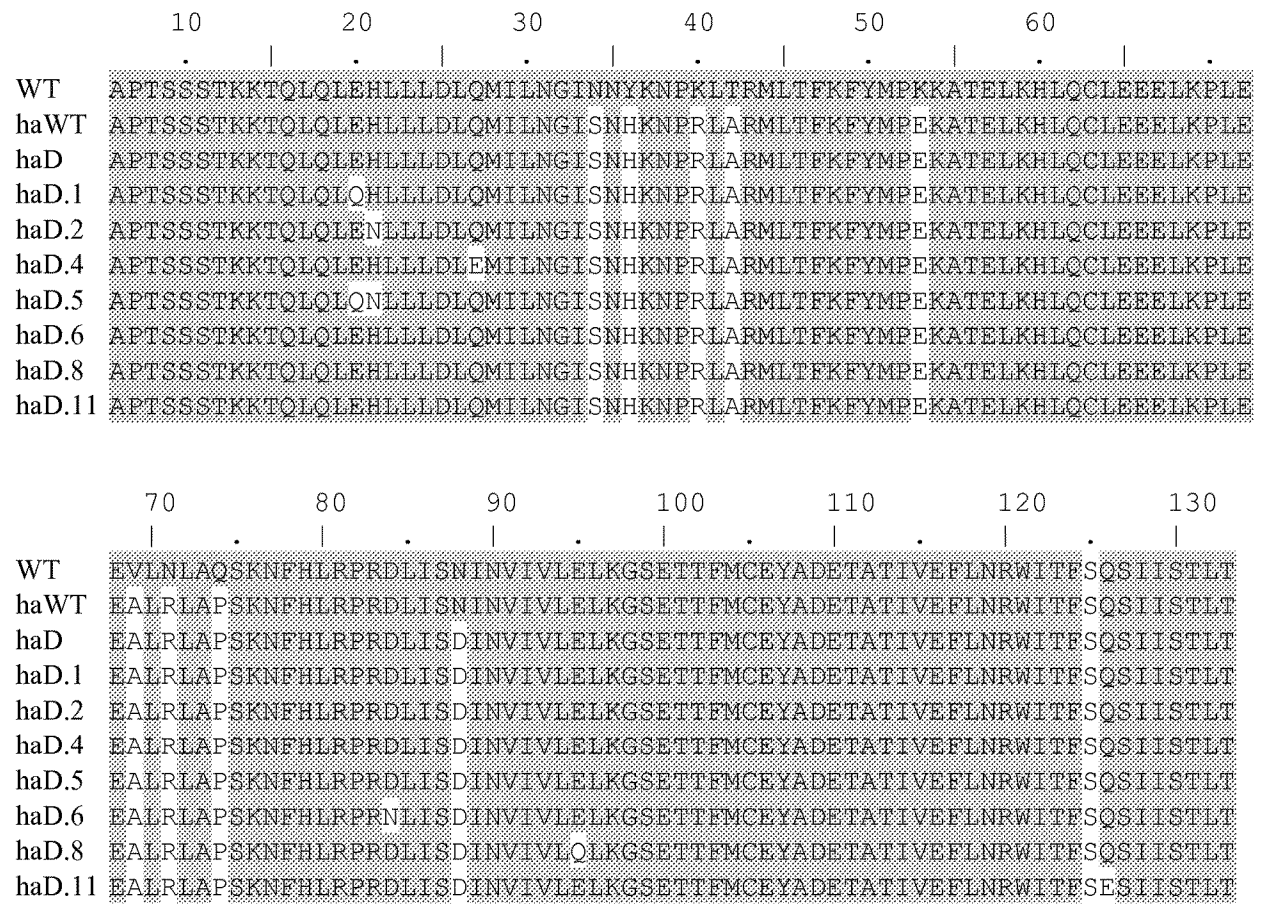

In certain embodiments, the IL-2 variant comprises a combination of mutations. Examples of IL-2 variants having a combination of mutations are provided in FIG. 1 and include haWT (SEQ ID NO:2), haD, (SEQ ID NO:3), haD.1 (SEQ ID NO:4), haD.2 (SEQ ID NO:5), haD.4 (SEQ ID NO:6), haD.5 (SEQ ID NO:7), haD.6 (SEQ ID NO:8), haD.8 (SEQ ID NO:9), and haD.11 (SEQ ID NO:10)d. In preferred embodiments, the IL-2 variant stimulates STAT5 phosphorylation in FOXP3-positive regulatory T cells but has reduced ability to induce STAT5 and AKT phosphorylation in FOXP3-negative T cells as compared to wild-type IL-2. Preferred variants having such properties include haD, haD.1, haD.2, haD.4, haD.5, haD.6, and haD.8.

The IL-2 variants may further comprise one or more mutations as compared to the wild-type IL-2 sequence that do not have an effect on the affinity for IL-2Rβ or IL-2Rγ, provided the IL-2 variant promotes the preferential proliferation, survival, activation or function of FOXP3$^+$ T-reg over that of other T cells that do not express FOXP3. In preferred embodiments, such mutations are conservative mutations.

The IL-2 variant may comprise one or more compounds to increase the serum-half-life of the IL-2 variant when administered to a patient. Such half-life extending molecules include water soluble polymers (e.g., polyethylene glycol (PEG)), low- and high-density lipoproteins, antibody Fc (monomer or dimer), transthyretin (TTR), and TGF-β latency associated peptide (LAP). Also contemplated are IL-2 variants comprising a combination of serum half-life extending molecules, such as PEGylated TTR (US Pat. Appl. Publ. No. 2003/0195154).

Methods of Making an Immunosuppressive IL-2 Variant

The immunosuppressive IL-2 variants can be produced using any suitable method known in the art, including those described in U.S. Pat. No. 6,955,807 for producing immunostimulatory IL-2 variants (incorporated herein by reference). Such methods include constructing a DNA sequence encoding the IL-2 variant and expressing those sequences in a suitably transformed host. This method will produce the recombinant variant of this invention. However, the variants may also be produced by chemical synthesis or a combination of chemical synthesis and recombinant DNA technology. Batch-wise production or perfusion production methods are known in the art. See Freshey, R. I. (ed), "Animal Cell Culture: A Practical Approach," 2nd ed., 1992, IRL Press. Oxford, England; Mather, J. P. "Laboratory Scaleup of Cell Cultures (0.5-50 liters)," Methods Cell Biolog 57: 219-527 (1998); Hu, W. S., and Aunins, J. G., "Large-scale Mammalian Cell Culture," Curr Opin Biotechnol 8: 148-153 (1997); Konstantinov, K. B., Tsai, Y., Moles, D., Matanguihan, R., "Control of long-term perfusion Chinese hamster ovary cell culture by glucose auxostat.," Biotechnol Prog 12:100-109 (1996).

In one embodiment of a recombinant method for producing a variant, a DNA sequence is constructed by isolating or synthesizing a DNA sequence encoding the wild type IL-2 and then changing one or more codons by site-specific mutagenesis. This technique is well known. See, e.g., Mark et. al., "Site-specific Mutagenesis Of The Human Fibroblast Interferon Gene", Proc. Natl. Acad. Sci. USA 81, pp. 5662-66 (1984); and U.S. Pat. No. 4,588,585, incorporated herein by reference.

Another method of constructing a DNA sequence encoding the IL-2 variant would be chemical synthesis. This for example includes direct synthesis of a peptide by chemical means of the protein sequence encoding for an IL-2 variant exhibiting the properties described herein. This method may incorporate both natural and unnatural amino acids at positions that affect the interactions of IL-2 with the IL2Rα, IL-2Rβ, or IL-2Rγ. Alternatively, a gene which encodes the desired IL-2 variant may be synthesized by chemical means using an oligonucleotide synthesizer. Such oligonucleotides are designed based on the amino acid sequence of the desired IL-2 variant, and preferably selecting those codons that are favored in the host cell in which the recombinant variant will be produced. In this regard, it is well recognized that the genetic code is degenerate—that an amino acid may be coded for by more than one codon. For example, Phe (F) is coded for by two codons, TTC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 variant, there will be many DNA degenerate sequences that will code for that IL-2 variant.

The DNA sequence encoding the IL-2 variant, whether prepared by site directed mutagenesis, chemical synthesis or other methods, may or may not also include DNA sequences that encode a signal sequence. Such signal sequence, if present, should be one recognized by the cell chosen for expression of the IL-2 variant. It may be prokaryotic, eukaryotic or a combination of the two. It may also be the signal sequence of native IL-2. The inclusion of a signal sequence depends on whether it is desired to secrete the IL-2 variant from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

Standard methods may be applied to synthesize a gene encoding an IL-2 variant. For example, the complete amino acid sequence may be used to construct a back-translated gene. A DNA oligomer containing a nucleotide sequence coding for an IL-2 variant may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis or another method), the DNA sequences encoding an IL-2 variant will be inserted into an expression vector and operatively linked to an expression control sequence appropriate for expression of the IL-2 variant in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host. The choice of expression control sequence and expression vector will depend upon the choice of host. A wide variety of expression host/vector combinations may be employed.

Any suitable host may be used to produce the IL-2 variant, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E. coli, Pseudomonas, Bacillus, Streptomyces*, fungi, yeast, insect cells such as *Spodoptera frugiperda* (Sf9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. For animal cell expression, CHO cells and COS 7 cells in cultures and particularly the CHO cell line CHO (DHFR-) or the HKB line are preferred.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vectors copy number, the ability to control that copy number, and the expression of any other proteins encoded by the vector, such as antibiotic markers, should also be considered. For example, preferred vectors for use in this invention include those that allow the DNA encoding the IL-2 variants to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304-19 (1982)) or glutamine synthetase ("GS") amplification (see, e.g., U.S. Pat. No. 5,122,464 and European published application 338,841).

The IL-2 variants may be glycosylated or unglycosylated depending on the host organism used to produce the variant. If bacteria are chosen as the host, then the IL-2 variant produced will be unglycosylated. Eukaryotic cells, on the other hand, will glycosylate the IL-2 variant, although perhaps not in the same way as native IL-2 is glycosylated. The IL-2 variant produced by the transformed host can be purified according to any suitable method. Various methods are known for purifying IL-2. See, e.g., Current Protocols in Protein Science, Vol. 2. Eds: John E. Coligan, Ben M. Dunn, Hidde L. Ploehg, David W. Speicher, Paul T. Wingfield, Unit 6.5 (Copyright 1997, John Wiley and Sons, Inc).

The biological activity of the IL-2 variants can be assayed by any suitable method known in the art. Such assays include those described in the Examples below.

Indications

Diseases, disorders, or conditions may be amenable to treatment with or may be prevented by administration of a T-reg-selective IL-2 variant to a subject. Such diseases, disorders, and conditions include, but are not limited to, inflammation, autoimmune disease, paraneoplastic autoimmune diseases, cartilage inflammation, fibrotic disease and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodosa, Wegener's granulomatosis, arteritis, polymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, Guillain-Barre disease, Type I diabetes mellitus, thyroiditis (e.g., Graves' disease), Addison's disease, Raynaud's phenomenon, autoimmune hepatitis, GVHD, transplantation rejection, and the like. In specific embodiments, pharmaceutical compositions comprising a therapeutically effective amount of a T-reg-selective IL-2 variant are provided.

The term "treatment" encompasses alleviation or prevention of at least one symptom or other aspect of a disorder, or reduction of disease severity, and the like. A T-reg-selective IL-2 variant need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient A T-reg-selective IL-2 variant in an amount and for a time sufficient to induce a sustained improvement over baseline of an indicator that reflects the severity of the particular disorder.

Pharmaceutical Compositions

In some embodiments, the invention provides pharmaceutical compositions comprising a therapeutically effective amount of one or a plurality of T-reg-selective IL-2 variants of the invention together with a pharmaceutically acceptable diluent, carrier, solubilizer, emulsifier, preservative, and/or adjuvant. In addition, the invention provides methods of treating a patient by administering such pharmaceutical composition. The term "patient" includes human and animal subjects.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolality, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, sucrose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapol); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Gennaro, ed.), 1990, Mack Publishing Company.

The therapeutically effective amount of T-reg-selective IL-2 variant-containing pharmaceutical composition to be employed will depend, for example, upon the therapeutic context and objectives. One skilled in the art will appreciate that the appropriate dosage levels for treatment will vary depending, in part, upon the molecule delivered, the indication for which the T-reg-selective IL-2 variant is being used, the route of administration, and the size (body weight, body surface or organ size) and/or condition (the age and general health) of the patient.

In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 0.1 µg/kg up to about 30 mg/kg, optionally from 1 µg/kg up to about 30 mg/kg or from 10 µg/kg up to about 5 mg/kg.

Dosing frequency will depend upon the pharmacokinetic parameters of the particular T-reg-selective IL-2 variant in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them.

The route of administration of the pharmaceutical composition is in accord with known methods, e.g., orally, through injection by intravenous, intraperitoneal, intracerebral (intraparenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

Combination Therapies

In further embodiments, T-reg-selective IL-2 variant is administered in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which a T-reg-selective IL-2 variant is administered at least once during a course of treatment that involves administering at least one other therapeutic agent to the patient.

In certain embodiments, a T-reg-selective IL-2 variant is administered in combination with an inhibitor of the PI3-K/AKT/mTOR pathway, e.g., rapamycin (rapamune, sirolimus). Inhibitors of this pathway in combination with IL-2 favor T-reg enrichment.

The invention having been described, the following examples are offered by way of illustration, and not limitation.

EXAMPLES

Example 1

Panel of IL-2 Mutants

To examine the potential for generating IL-2 variants with reduced capacity to stimulate FOXP3$^-$ CD25$^+$ "effector" T cells (T-eff) but not T-reg, a series of IL-2 mutants was generated in which amino acids predicted to interact with the IL-2Rβ and/or IL-2Rγ chain were altered. These variants also contained a set of previously described mutations that conferred high affinity for CD25 (variant "2-4" in Rao et al., *Biochemistry* 44, 10696-701 (2005)). This series of variants is shown in FIG. 1. Variant haWT contained only the mutations that contributed to the high affinity for CD25. Variants haD, haD.1, haD.2, etc, also contained mutations predicted to alter interactions with IL-2Rβ and/or IL-2Rγ. In all assays, variant haD.11 was not capable of inducing any signal or altering any cellular phenotype and, as such, served as a control for CD25 binding without IL-2R signaling. All the IL-2 variants contained the C125S mutation for improved manufacturability and terminated with FLAG and HIS-tag sequences (DYKDDDDKGSSHHHHHH) (SEQ ID NO:11)

Several assays were used to assess the ability of the IL-2 variants to induce signaling events and T cell growth. These included assays to detect:
1. Growth and survival of T cell subsets and measurement of FOXP3 expression.
2. Cell signaling (e.g. detection of phosphorylated STAT5 and AKT using flow cytometric and ELISA-based methods).

Example 2

Enrichment of FOXP3$^+$ Cells and Retention of FOXP3 Upregulation During Long Term T Cell Culture Total PBMC were activated in 24-well plates at 4×10$^6$ cells per well with 100 ng/ml anti-CD3 (OKT3). On day 3 of culture, cells were washed 3 times and rested in fresh media for 3 days. Cells were then washed and seeded in 96 well flat-bottom plates with IL-2 variants at either 10 nM or 100 pM. Three days later cells were counted and analyzed by flow cytometry. (FIG. 2A)

Figure 2B:
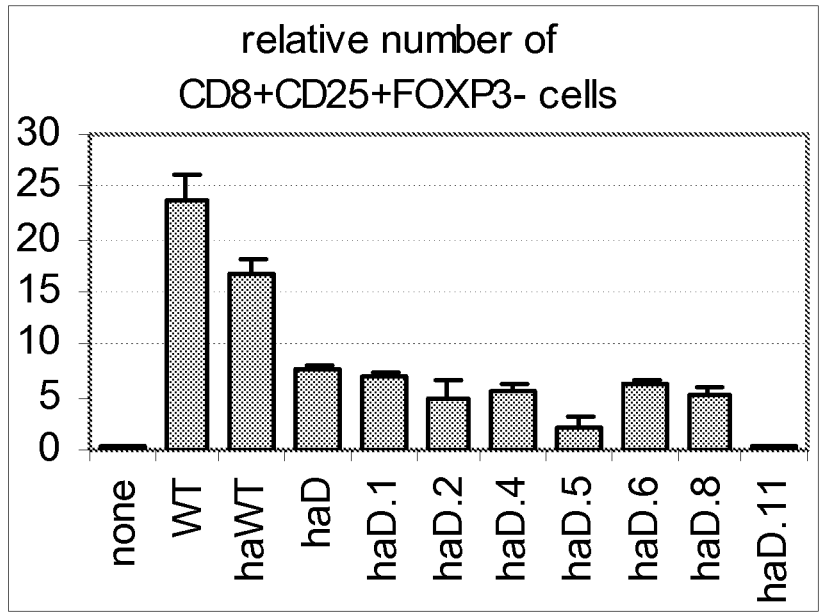
Figure 2B:
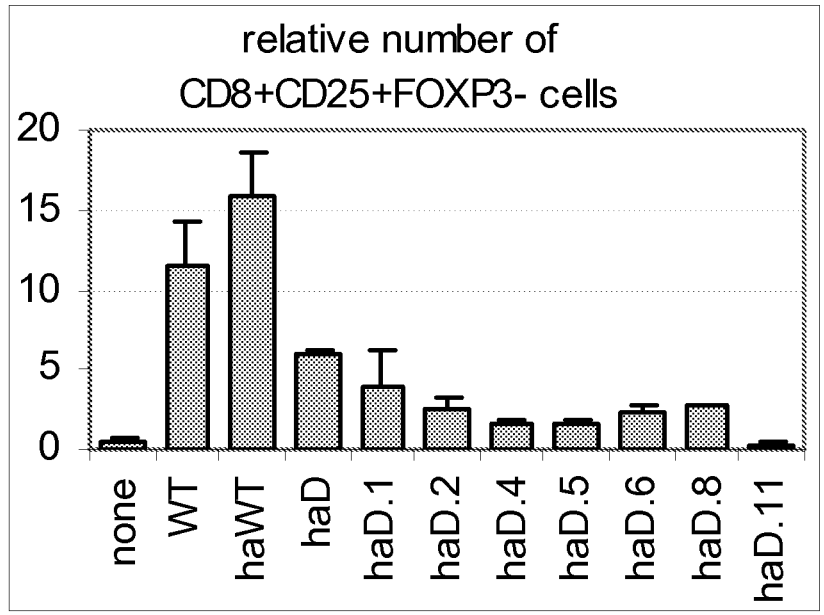
Figure 2C:
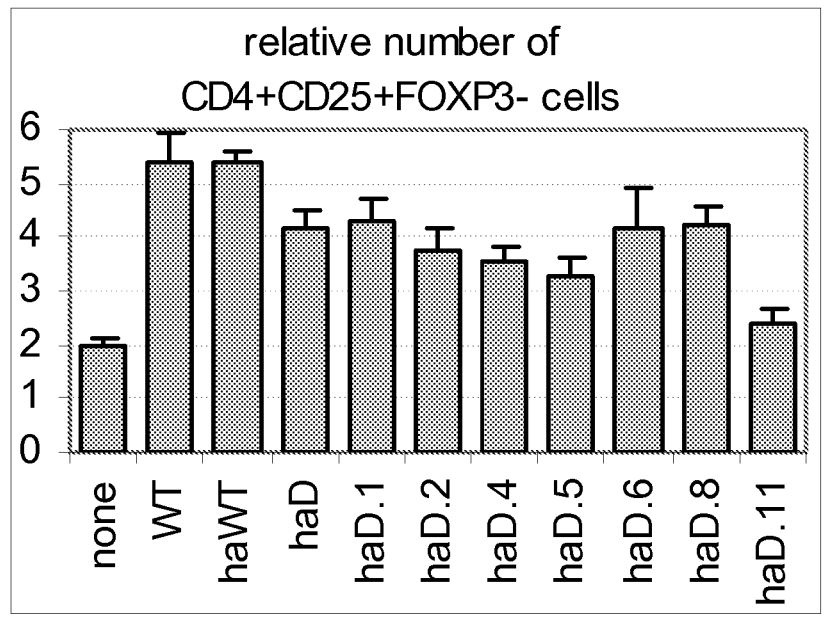
Figure 2C:
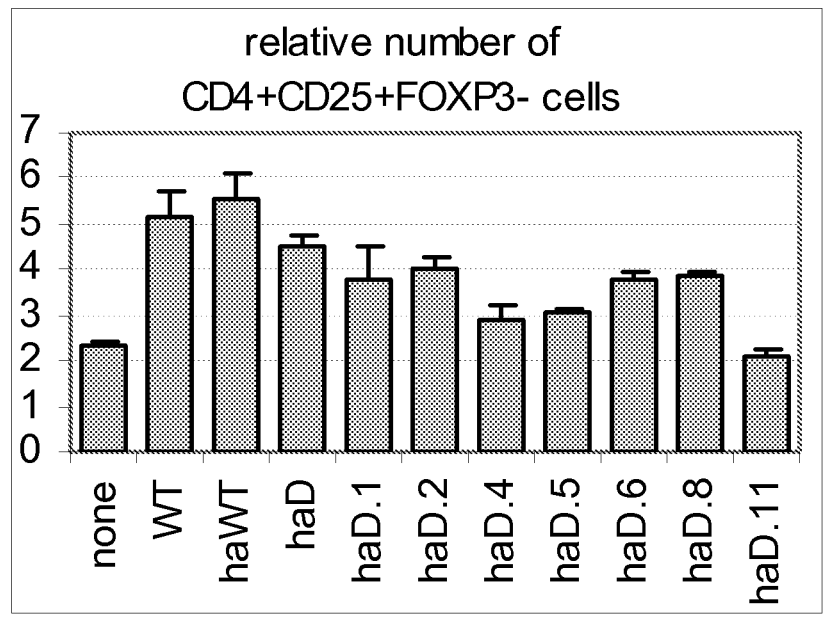
Figure 2D:
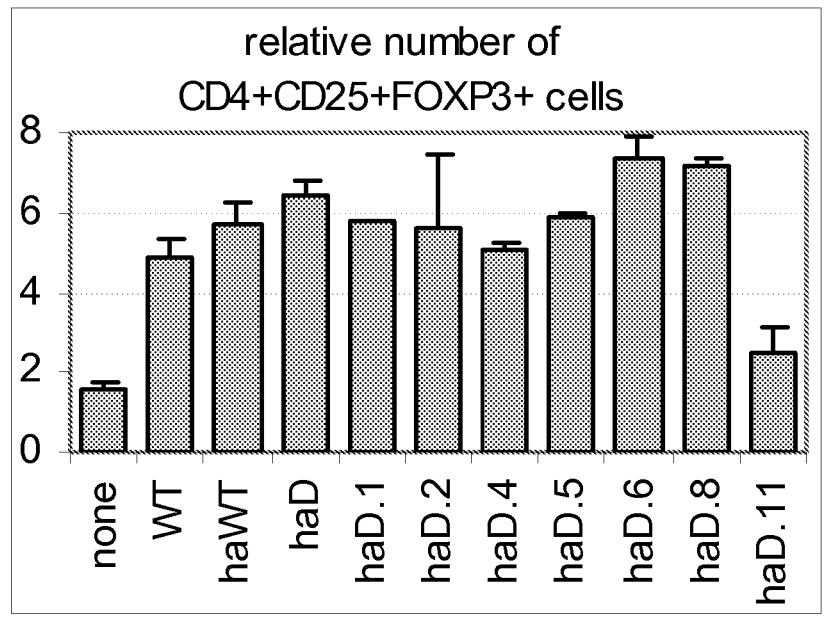
Figure 2D:
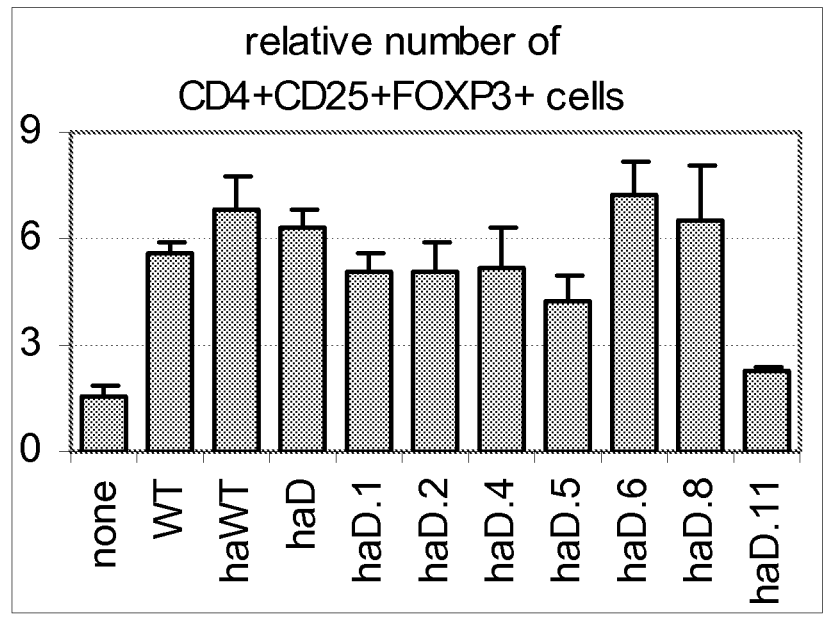
Figure 2E:
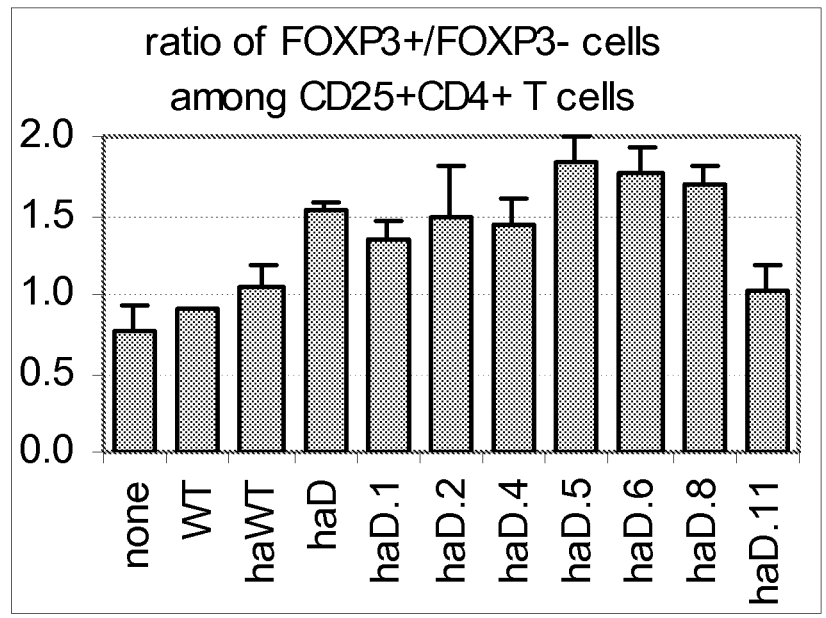
Figure 2E:
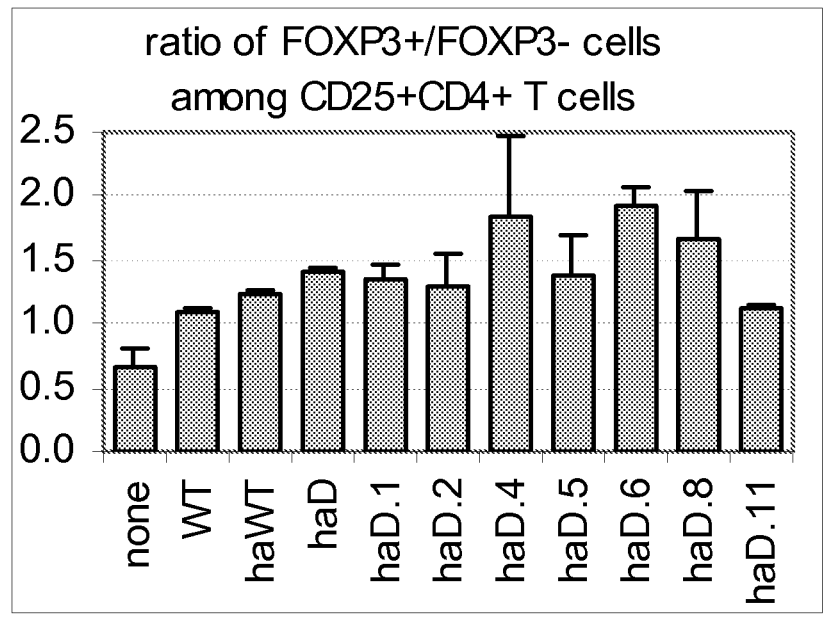
Figure 2F:
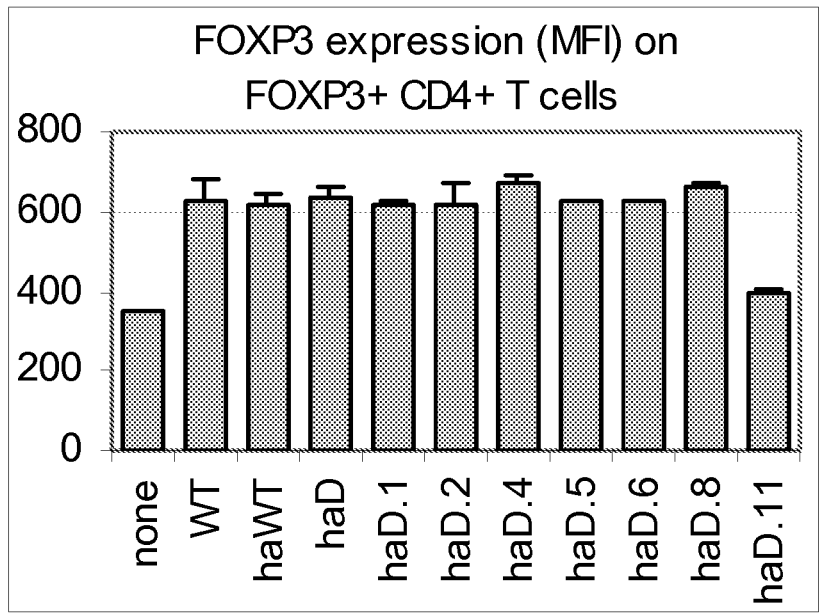
Figure 2F:
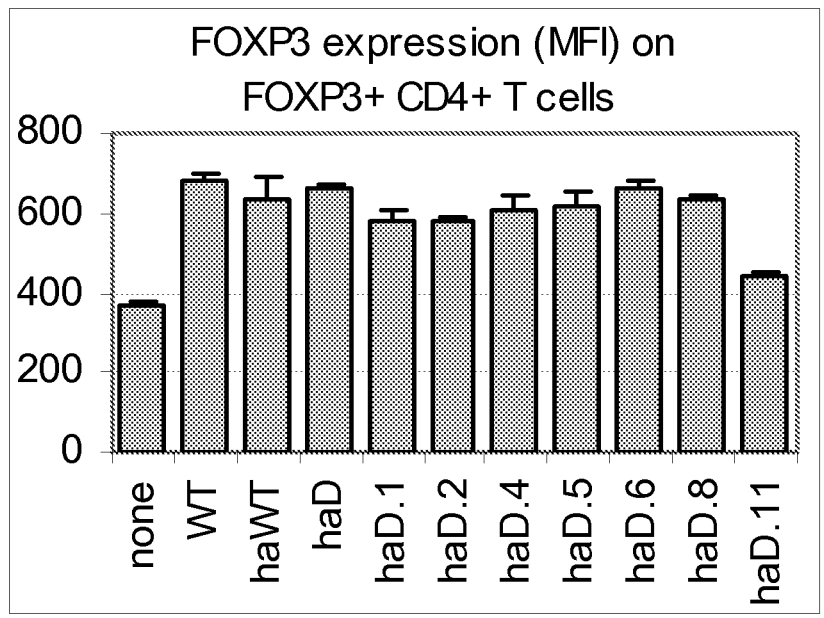
Figure 3:
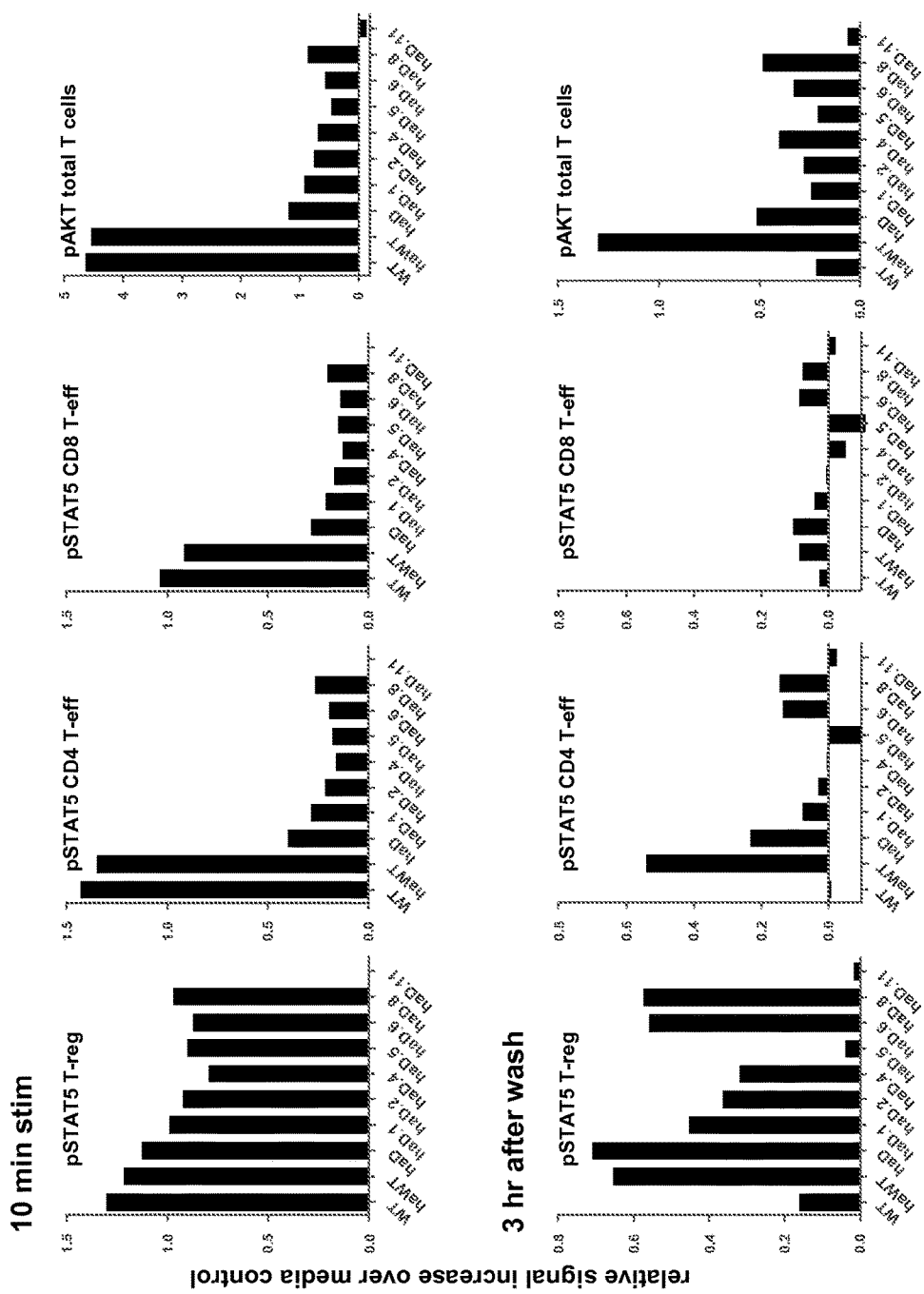
FIG. 3. IL-2 muteins stimulate phospho-STAT5 in T-reg but are inefficient at stimulating signals in other T cells. T cells were stimulated with IL-2 as described in Example 3. Phospho-STAT5 was measured by flow cytometry and phospho-AKT was measured by ELISA (MesoScale Discovery). Abbreviations are as follows: T-reg, FOXP3+CD4+ T cells; CD4 T-eff, CD4+CD25+FOXP3− "effector" T cells; CD8 T-eff, CD8+CD25+FOXP3− "effector" T cells.

As expected, CD8+CD25+ T cells were especially responsive to WT IL-2 and variant haWT, however, all variants that contained mutated IL-2Rβ and/or γ contact residues were very inefficient at promoting accumulation of activated CD8+CD25+ T cells (FIG. 2B). A similar trend was observed for CD4+CD25+FOXP3− T cells (FIG. 2C). In contrast, the growth/survival of FOXP3+ CD4+ T cells was stimulated by several IL-2 variants to a degree similar to that of WT IL-2 (FIG. 2D). As a result, the ratio of FOXP3+ to FOXP3− T cells among CD4+ CD25+ T cells was increased by several IL-2 variants with IL-2Rβγ-contact residue mutations (FIG. 2E). Furthermore, the mutations did not impair IL-2-stimulated FOXP3 upregulation in T-reg (FIG. 2F).

Example 3

<220> FEATURE:
<223> OTHER INFORMATION: IL-2 Variant

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Ser Asn His Lys
            20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
    50                  55                  60

Pro Leu Glu Glu Ala Leu Arg Leu Ala Pro Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 3
<211> LENGTH: 133
<212> TYPE: PRT
<213> ORGANISM: Artificial
<220> FEATURE:
<223> OTHER INFORMATION: IL-2 Variant

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Ser Asn His Lys
            20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
    50                  55                  60

Pro Leu Glu Glu Ala Leu Arg Leu Ala Pro Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 4
<211> LENGTH: 133
<212> TYPE: PRT
<213> ORGANISM: Artificial
<220> FEATURE:
<223> OTHER INFORMATION: IL-2 Variant

<400> SEQUENCE: 4

Ala Pro Thr Ser Ser Ser Thr Lys Lys Thr Gln Leu Gln Leu Gln His
1               5                   10                  15

Leu Leu Leu Asp Leu Gln Met Ile Leu Asn Gly Ile Ser Asn His Lys
            20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
    50                  55                  60

Pro Leu Glu Glu Ala Leu Arg Leu Ala Pro Ser Lys Asn Phe His Leu
65                  70                  75                  80

Arg Pro Arg Asp Leu Ile Ser Asp Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 5
<211> LENGTH: 133
<212> TYPE: PRT
<213> ORGANISM: Artificial
<220> FEATURE:
<223> OTHER INFORMATION: IL-2 Variant

<400> SEQUENCE: 5

Ala Pro Thr Ser Ser Ser Thr Lys Lys Thr Gln Leu Gln Leu Glu Asn
1               5                   10                  15

Leu Leu Leu Asp Leu Gln Met Ile Leu Asn Gly Ile Ser Asn His Lys
            20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
    50                  55                  60

Pro Leu Glu Glu Ala Leu Arg Leu Ala Pro Ser Lys Asn Phe His Leu
65                  70                  75                  80

Arg Pro Arg Asp Leu Ile Ser Asp Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 6
<211> LENGTH: 133
<212> TYPE: PRT
<213> ORGANISM: Artificial
<220> FEATURE:
<223> OTHER INFORMATION: IL-2 Variant

<400> SEQUENCE: 6

Ala Pro Thr Ser Ser Ser Thr Lys Lys Thr Gln Leu Gln Leu Glu His
1               5                   10                  15

Leu Leu Leu Asp Leu Glu Met Ile Leu Asn Gly Ile Ser Asn His Lys
            20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
 50                  55                  60

Pro Leu Glu Glu Ala Leu Arg Leu Ala Pro Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 7
<211> LENGTH: 133
<212> TYPE: PRT
<213> ORGANISM: Artificial
<220> FEATURE:
<223> OTHER INFORMATION: IL-2 Variant

<400> SEQUENCE: 7

Ala Pro Thr Ser Ser Ser Thr Lys Lys Thr Gln Leu Gln Leu Gln Asn
 1               5                  10                  15

Leu Leu Leu Asp Leu Gln Met Ile Leu Asn Gly Ile Ser Asn His Lys
                20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys
 50                  55                  60

Pro Leu Glu Glu Ala Leu Arg Leu Ala Pro Ser Lys Asn Phe His Leu
 65                  70                  75                  80

Arg Pro Arg Asp Leu Ile Ser Asp Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 8
<211> LENGTH: 133
<212> TYPE: PRT
<213> ORGANISM: Artificial
<220> FEATURE:
<223> OTHER INFORMATION: IL-2 Variant

<400> SEQUENCE: 8

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Ser Asn His Lys
                20                  25                  30

Asn Pro Arg Leu Ala Arg Met Leu Thr Phe Lys Phe Tyr Met Pro Glu
        35                  40                  45

Lys Ala Thr Glu Leu Lys His Leu Gln Cys Leu Glu Glu Glu Leu Lys

```
                    50                  55                  60

Pro Leu Glu Glu Ala Leu Arg Leu Ala Pro Ser Lys Asn Phe His Leu
 65                  70                  75                  80

Arg Pro Arg Asn Leu Ile Ser Asp Ile Asn Val Ile Val Leu Glu Leu
                     85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 9
<211> LENGTH: 133
<212> TYPE: PRT
<213> ORGANISM: Artificial
<220> FEATURE:
<223> OTHER INFORMATION: IL-2 Variant

<400> SEQUENCE: 9

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Ser Asn His Lys
                 20                  25                  30

Asn Pro Arg Leu Ala Arg Met Leu Thr Phe Lys Phe Tyr Met Pro Glu
             35                  40                  45

Lys Ala Thr Glu Leu Lys His Leu Gln Cys Leu Glu Glu Glu Leu Lys
 50                  55                  60

Pro Leu Glu Glu Ala Leu Arg Leu Ala Pro Ser Lys Asn Phe His Leu
 65                  70                  75                  80

Arg Pro Arg Asp Leu Ile Ser Asp Ile Asn Val Ile Val Leu Gln Leu
                     85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 10
<211> LENGTH: 133
<212> TYPE: PRT
<213> ORGANISM: Artificial
<220> FEATURE:
<223> OTHER INFORMATION: IL-2 Variant

<400> SEQUENCE: 10

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Ser Asn His Lys
                 20                  25                  30

Asn Pro Arg Leu Ala Arg Met Leu Thr Phe Lys Phe Tyr Met Pro Glu
             35                  40                  45

Lys Ala Thr Glu Leu Lys His Leu Gln Cys Leu Glu Glu Glu Leu Lys
 50                  55                  60

Pro Leu Glu Glu Ala Leu Arg Leu Ala Pro Ser Lys Asn Phe His Leu
 65                  70                  75                  80
```

```
Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Glu Ser Ile
        115                 120                 125

Ile Ser Thr Leu Thr
    130

<210> SEQ ID NO 11
<211> LENGTH: 17
<212> TYPE: PRT
<213> ORGANISM: Artificial
<220> FEATURE:
<223> OTHER INFORMATION: FLAG-His

<400> SEQUENCE: 11

Asp Tyr Lys Asp Asp Asp Lys Gly Ser Ser His His His His His
1               5                   10                  15

His
```

What is claimed is:

1. A method of treating graft versus host disease in a subject, said method comprising administering to a subject in need thereof a therapeutically effective amount of an IL-2 variant comprising a sequence of amino acids that differs from SEQ ID NO: 1 only at one or more of residues E15, H16, Q22, D84, N88, or E95, wherein said IL-2 variant selectively promotes FOXP3-positive regulatory T cell growth or survival in vitro.

2. The method of claim 1, wherein the IL-2 variant induces STAT5 phosphorylation in ex vivo FOXP3-positive T cells comprising a functional IL-2 receptor complex but has a reduced ability to induce phosphorylation of STAT5 in FOXP3-negative T cells.

3. The method of claim 1, wherein the IL-2 variant is conjugated to a chemical or polypeptide that extends the serum half-life of said IL-2 variant in vivo.

* * * * *